United States Patent [19]

Kaczmarek et al.

[11] Patent Number: 4,973,323

[45] Date of Patent: Nov. 27, 1990

[54] OSTOMY APPLIANCE

[75] Inventors: Lynn M. Kaczmarek, Buffalo Grove; Paul O. Kay, Barrington; George M. Nowak, Lake Villa; Barry L. Schneider, Deerfield, all of Ill.

[73] Assignee: Hollister Incorporated, Libertyville, Ill.

[21] Appl. No.: 402,483

[22] Filed: Sep. 1, 1989

[51] Int. Cl.⁵ .................... A61M 31/00; A61F 5/44; A61F 5/448

[52] U.S. Cl. .................. 604/339; 604/277; 604/332; 604/336; 604/337; 604/338; 604/342; 604/344; 604/317

[58] Field of Search .................. 604/277, 332–345

[56] References Cited

U.S. PATENT DOCUMENTS

| | | | |
|---|---|---|---|
| 4,350,785 | 9/1982 | Habib | 604/339 |
| 4,610,676 | 9/1986 | Schneider et al. | 604/339 |
| 4,610,677 | 9/1986 | Mohiudoin | 604/339 |
| 4,808,173 | 2/1989 | Kay | 604/339 |
| 4,834,731 | 5/1989 | Nowak | 604/339 |

FOREIGN PATENT DOCUMENTS 2193439 2/1988 United Kingdom ............... 604/332

Primary Examiner—Alan Cannon
Assistant Examiner—Robert Clarke
Attorney, Agent, or Firm—Tilton, Fallon, Lungmus

[57] ABSTRACT

As ostomy appliance having a collection pouch and a flexible faceplate, the faceplate including an outer ring of thin, microporous sheet material and an inner ring of flexible, thermoplastic film impervious to gases and body fluids. The outer microporous ring surrounds the inner ring so that their adjacent margins overlap and are sealed to each other. The faceplate also includes a barrier ring secured to the inner marginal portion of the microporous ring on the side opposite from the attachment of the impervious inner ring. A fluid-impervious annular seal is provided between the impervious inner ring and the barrier ring at a location radially inwardly from the microporous ring, thereby securing the parts together and isolating the inner margin of the microporous ring from contact by stomal fluids. In preferred embodiments, the faceplate may include a relatively rigid, convex pressure ring and the impervious inner ring may extend a substantial distance radially inwardly from the seal with the inner margin of that ring secured to an outwardly extending thermoplastic web that in turn is connected to a faceplate coupling ring.

12 Claims, 2 Drawing Sheets

OSTOMY APPLIANCE

BACKGROUND AND SUMMARY

Co-owned U.S. Pat. No. 4,419,100 discloses an ostomy appliance of two main parts detachably connected by a pair of semi-rigid coupling rings. One part consists of a pouch on which one of the coupling rings is mounted, the other takes the form of a faceplate to which the other of the rings is connected by means of a flexible annular web. The web allows limited floating action between the second coupling ring and the faceplate, thereby facilitating attachment and detachment of the rings without causing wearer discomfort and allowing conformity of the flexible faceplate to a wearer's body without objectionable resistance from the semi-rigid rings.

U.S. Pat. No. 4,834,731 discloses an ostomy appliance having a convex pressure ring assembly and, in one embodiment (FIG. 7) a web is also utilized to connect a faceplate, in which a convex pressure ring is provided, with a semi-rigid coupling ring, thereby utilizing the floating ring feature of the first-mentioned patent. Both patents also disclose that the faceplates may be formed largely of gas-penetrable, but water-resistant microporous sheet material. Reference is made to co-owned U.S. Pat. No. 4,213,458 which also shows and describes microporous faceplate constructions with particular emphasis on the coactive use of a thin, flexible attaching ring for securing a microporous faceplate to a pouch in a manner that converts peeling forces to shearing forces and thereby reduces the possibilities that the microporous faceplate might become torn in use.

A microporous faceplate is considered superior to a non-porous faceplate because it does not prevent cutaneous respiration and, since water vapor is allowed to escape, such a faceplate may remain in place for longer intervals without tissue necrosis and other complications. A gas-permeable pressure-sensitive adhesive is used to secure such a faceplate to the peristomal surfaces of the skin. While conventional adhesives used for that purpose are not water-soluble in the ordinary sense, they are degraded by contact with water and we have found that with some microporous faceplate constructions there is a risk that stomal fluid may wick through the microporous matrix and adversely affect the adhesive seal. Moreover, if such conditions exist, then there is also the possibilities of fluid leakage in planar pathways through the microporous material of a faceplate, an obviously undesirable circumstance.

An important aspect of this invention therefore lies in providing a microporous faceplate construction which achieves the advantages of prior constructions, including the advantages disclosed in some or all of the aforementioned patents, while at the same time providing an improved construction for insuring that the inner margin of a microporous ring will remain isolated from contact with stomal fluid when the ostomy appliance is in use. In addition to its durability and outstanding leak-resistant properties, such a construction may also provide additional advantages such as, for example, increasing the "floating" action of a faceplate coupling ring, thereby increasing security, patient comfort and ease of attachment.

Briefly, the ostomy appliance includes a collection pouch formed of plastic film having a wall provided with a stoma opening. A flexible and generally planar faceplate is provided for adhesively attaching the pouch to the peristomal skin surfaces of a wearer. In its simplest form, the faceplate includes an outer ring of thin, microporous sheet material and an inner ring formed of a thermoplastic film that is impervious to gases and body fluids. The rings have coaxial openings aligned with the stoma opening of the pouch with the opening of the microporous ring being substantially larger than that of the inner impervious ring. The impervious inner ring has its proximal or bodyside surface along its outer margin secured to the distal surface of the microporous ring adjacent its inner margin. An adhesive barrier ring is secured to the proximal surface of the microporous ring and extends radially inwardly from the inner margin of the microporous ring, and a fluid-impervious annular seal is provided between the proximal surface of the inner ring and the inwardly-extending portion of the barrier ring for securing such rings together and for isolating the inner margin of the microporous ring, and the pressure-sensitive adhesive layer on the proximal surface of that ring, from contact by stomal fluids.

In different embodiments of the invention, the seal may take the form of a sealant ring or of an annular heat seal. If a sealant ring is provided, it may also sealingly and adhesively engage the microporous ring along its inner margin. Most advantageously, the seal is spaced a substantial distance radially outwardly from the inner margin of the impervious inner ring. A sealant ring is preferably formed of a hot melt sealant, particularly one that is deformable and elastically recoverable.

Where the sealant ring is spaced a substantial distance radially outwardly from the inner margin of the impervious inner ring, that inner margin may be sealed to the inner portion of an annular thermoplastic web which in turn has its outer margin attached to a relatively rigid (or semi-rigid) faceplate coupling ring. That coupling ring is therefore connected to the faceplate in a "floating" relationship that permits a user to insert his/her fingers between the two during a coupling operation. The floating ring construction performs a major function in allowing the flexible faceplate to conform with the contours of a wearer's body without resistance from the relatively rigid coupling ring(s) attached to that faceplate.

In one form of the invention the barrier ring, in addition to including a layer of soft, deformable, moisture-absorbing skin barrier material having both wet and dry tack, has a layer of soft liquid and gas impermeable thermoplastic foam (or other thermoformable material) and a relatively rigid convex pressure ring positioned with its convex surface facing proximally and contacting the thermoplastic foam. In such a construction, the adhesive sealant ring or annular heat seal may also engage or include the distal surface of the convex pressure ring to provide a secure bond between the different rings of the faceplate.

Other features, objects, and advantages will become apparent from the specification and the drawings.

DRAWINGS

DETAILED DESCRIPTION OF PREFERRED EMBODIMENTS

Figure 1:
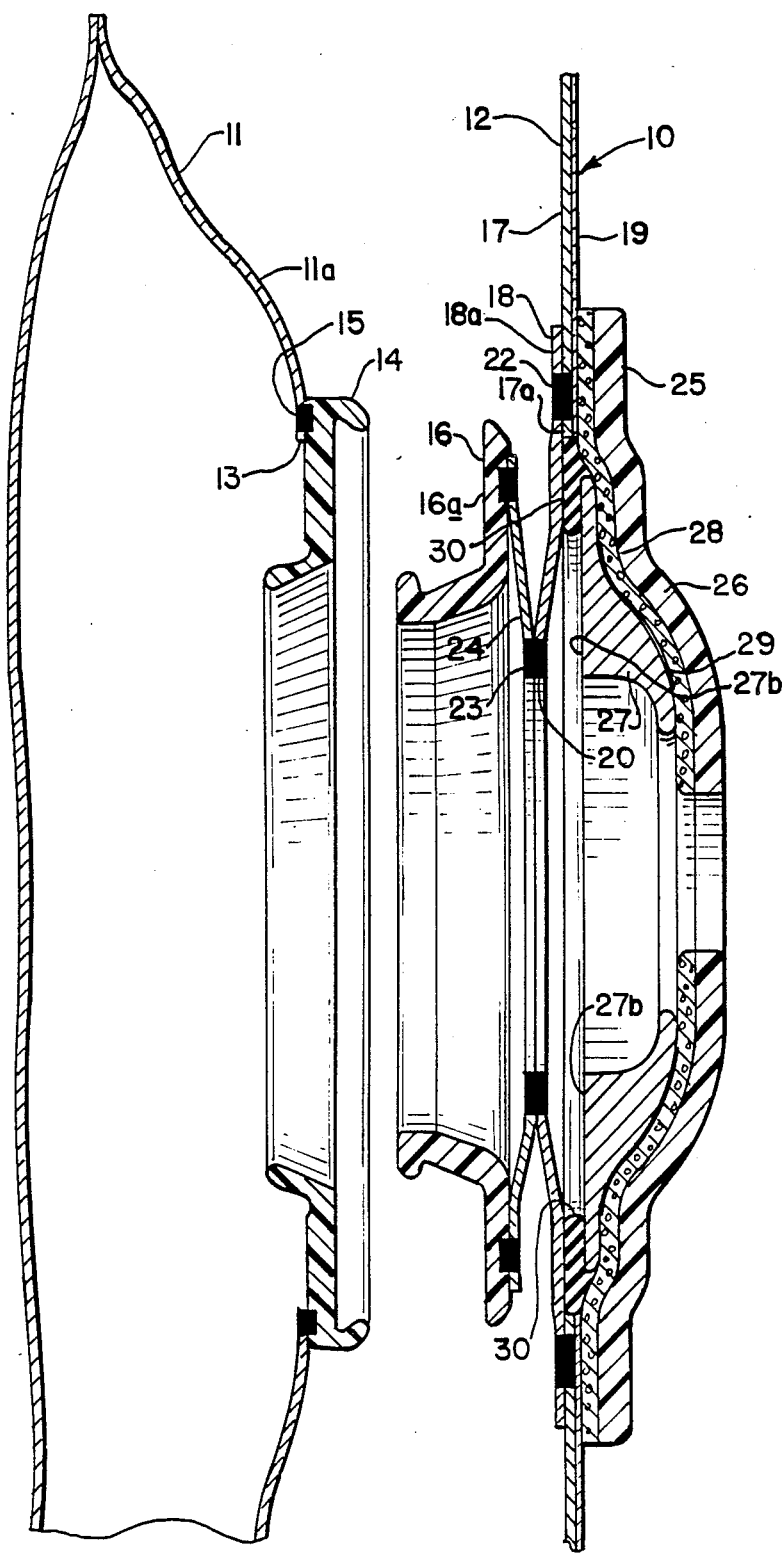
FIG. 1 is a fragmentary vertical sectional view of a two-piece ostomy appliance embodying the present invention, the two parts of the appliance being shown in separated condition for clarity of illustration.

The construction depicted in FIG. 1 is similar in many respects to the convex pressure ring assembly illustrated in FIG. 7 of co-owned U.S. Pat. No. 4,834,731, the disclosure of which is incorporated by reference herein. Ostomy appliance 10 includes a collection pouch 11 and a faceplate assembly 12. Pouch wall 11a, referred to as a proximal wall or panel because it is in closer proximity to the patient when the appliance is worn, is provided with a stoma-receiving opening 13 near its upper end. A pouch coupling ring 14 is heat sealed at 15 to the wall 11a of the pouch about the perimeter of opening 13. A second coupling ring 16 carried by faceplate 12 is formed and constructed to mate with pouch ring 14 for detachably joining the two parts of the appliance together.

The flexible plastic coupling rings 14 and 16 are similar in structure and operation to those described in U.S. Pat. No. 4,610,678, the disclosure of which is incorporated by reference herein. The advantage of such a construction is that a user wearing the two-piece appliance may remove pouch 11 and replace it with a fresh pouch while leaving faceplate 12 attached to the body wall. While FIG. 1 illustrates one type of two-piece coupling, it is to understood that other types of detachable coupling ring assemblies may be used to permit attachment and detachment of the faceplate and pouch.

The faceplate assembly 12 includes an outer ring 17 and an inner ring 18. Outer ring 17 is formed of a nonwoven microporous sheet material of the type disclosed in U.S. Pat. No. 4,213,458. A non-woven microporous material of polyester fibers is believed particularly suitable. The microporous material should have gas and water vapor transmission characteristics sufficiently high to permit the release of water vapor and gases from the skin at a rate high enough to avoid the retention and accumulation of liquid on the surface of the skin covered by the microporous outer ring. The proximal surface of the microporous ring is covered by a layer 19 of pressure-sensitive adhesive. While a conventional medical-grade acrylic adhesive has been found particularly effective, any suitable pressure-sensitive adhesive that is non-allergenic and gas/vapor permeable may be used.

The inner ring 18 is formed of a sheet of thin, flexible, thermoplastic material capable of being heat sealed to the microporous material of outer ring 17. Ethyl vinyl acetate is particularly effective for that purpose, but other thermoplastic materials might be used and may even be preferable if, for example, a microporous ring of different composition is used.

The inner and outer rings have coaxial openings 20 and 21 aligned with each other and with the stoma opening 13 of the pouch 11 when the appliance is assembled. It will be observed from FIGS. 1 and 2 that impervious ring 18 has its outer marginal portion 18a heat sealed or otherwise permanently secured at 22 to the inner marginal portion 17a of microporous ring 17. It will also be noted that the two rings are arranged so that marginal portion 18a of the impervious ring is disposed on the distal side of the inner marginal portion 17a of the microporous ring.

At its inner limits, the impervious inner ring 18 is heat sealed at 23 to a thin, flexible, annular thermoplastic web 24 that extends radially outwardly from the annular heat sealed zone. Near its outer margin, the web is in turn heat sealed to the radially outwardly extending annular flange of 16a of faceplate coupling ring 16. While the web 24 may be formed of any tough and durable thermoplastic material capable of being heat sealed to the inner marginal portion of impervious ring 18, low density polyethylene coextruded with a coextensive layer or core of polyvinylidene chloride, known under the designation Saranex, from Dow Chemical Company, Midland, Mich., has been found particularly effective.

Figure 2:
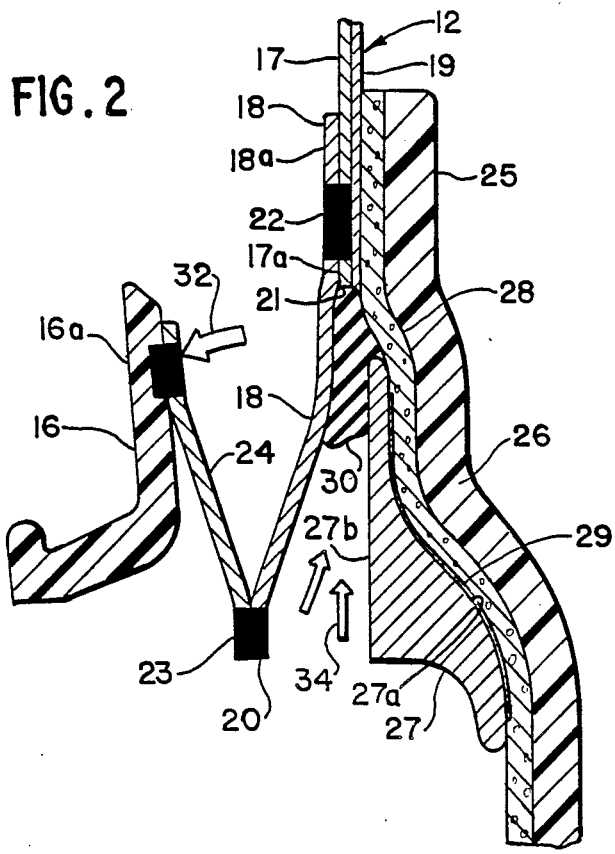
FIG. 2 is an enlarged fragmentary sectional view showing details of the structure of FIG. 1 and also illustrating the relationship of parts when the faceplate coupling ring is urged away from the faceplate.

Another component of the faceplate assembly 12 takes the form of a barrier ring 25 which, in the embodiment of FIGS. 1 and 2, consists of a proximal skin barrier layer 26, a distal convex pressure ring 27, and a resilient thermoformable layer 28 interposed between the two. Most advantageously, the intermediate thermoformable layer or ring is formed of soft, flexible, and resilient thermoplastic foam that is both liquid and gas impermeable. While any thermoplastic foam having such characteristics may be used, particularly effective results have been obtained using a closed-cell polyethylene foam having a general thickness within the range of about 0.3 to 10 mm., all as described in aforementioned U.S. Pat. No. 4,834,731. The resilient foam provides a cushion between the skin barrier layer 26 and the inner marginal portion 17a of microporous ring 17, and also between the skin barrier layer and convex pressure ring 27, and restrains cold flow of the skin barrier material.

The protective skin barrier layer or ring 26 is formed of a soft, pliable, water-absorbing material having both dry and wet tack. A variety of such compositions are known in the art and may be used. Karaya-glycerin formulations, and mixtures of polyacrylamide resin and other polyols and mixtures of elastomers and hydrocolloids may be used. Reference may be had to U.S. Pat. No. 4,477,325 and 4,496,357 for a discussion of prior skin barrier compositions and a disclosure of additional compositions having advantages which may also be utilized here.

The foam layer or ring 28 is secured to the skin barrier layer by the adhesive properties of the skin barrier material and to the proximal surface of convex pressure ring 27 by means of a pressure-sensitive adhesive coating 29. The composition of the adhesive may be the same as that of adhesive coating 19 on the microporous outer ring 17.

As clearly depicted in FIGS. 1 and 2, the pressure ring 27 has a generally convex proximal surface 27a and a planar distal surface 27b. Ring 27 is relatively rigid, the term "relatively rigid" here being used to mean that the ring retains its distinctive shape under normal conditions of use. While various materials may be used for the pressure ring or support ring 27, rigid or semi-rigid plastics such as polypropylene, polyethylene, or polystyrene are considered particularly suitable.

Disposed between the impervious inner ring 18 and the barrier ring 25 in a zone radially inboard of heat seal 22 is sealing means in the form of a sealant ring 30. The sealant ring is thermoplastic and preferably takes the form of a hot melt sealant. Various hot melt sealant compositions are known and available, some being relatively rigid and others being flexible and relatively elastic. Any suitable heat sealant composition may be used, either rigid or flexible, as long as it is capable of forming a liquid-proof (waterproof) seal with the various elements of the faceplate assembly that it contacts; however, a flexible hot melt sealant, one that may also have pressure-sensitive characteristics, is believed preferable. One such material is available under the designation HM6515 from H. B. Fuller Company, St. Paul, Minn. Others are designated as 34—2881 from National Starch & Chemical Corporation, Bridgewater, N.J. and 84116 from Swift Adhesives Division, Reichold Chemicals, Inc., Chicago, Ill. As well-known in the art, hot melt sealants, even those that have pressure-sensitive adhesive characteristics when cool, in effect form heat seals or fusion seals with compatible surfaces when applied in a molten state to such surfaces. Hence, even if the sealant has pressure-sensitive adhesive properties when cool, the bond with the surface of application is more of a heat seal bond than an adhesive bond.

While sealant ring 30 is located radially inboard from sealing zone 22, it is nevertheless a substantial distance outboard from the heat seal 23 between the inner marginal portion of impervious ring 18 and thermoplastic web 24. Therefore, the inner ring 18 and web 24 coact to provide a flexible and axially-expandable connection between faceplate coupling ring 16 and the remainder of the faceplate assembly. Should forces be exerted to urge the coupling ring distally away from assembly 12 in the direction indicated by arrow 31 (FIG. 2), the peripheral spacing between the faceplate and the coupling ring may be increased. Such axial displacement allows a user to insert his/her fingers between the faceplate and the coupling ring when that ring is to be urged into latching engagement with pouch ring 14. Because the floating connection between the ring 16 and faceplate assembly 12 is created by two flexible elements joined together along their inner margins (inner ring 18 and web 24), the floating action is effectively enhanced. It is to be understood, however, that when no forces are exerted in the direction of arrow 32, both the web 24 and inner ring 18 tend to assume contiguous positions with their facing surfaces in contact, or approaching contact, with each other. Thus, the condition shown in FIG. 1 with the surfaces of web 24 and inner ring 18 spaced apart, is exaggerated for clarity of illustration.

The drawings depict a preferred construction in which the sealant ring 30 is in fluid-tight sealing contact with four elements: inner ring 18, microporous outer ring 17, resilient foam layer 28, and semi-rigid support ring 27. While such an arrangement is highly desirable, it is not absolutely essential that the sealant ring 30 be directly bonded to the microporous ring 17. What is critical is that the sealant ring be sealingly joined to both the inner impervious ring 18 and the distal side of barrier ring 25 (i.e., either one or both of foam layer 28 and support ring 27) so that stomal fluids flowing outwardly as indicated by arrows 34 in FIG. 2 are blocked from reaching the inner margins of microporous ring 17 and its adhesive coating 19. The sealant ring therefore performs the dual functions of securely connecting barrier ring and inner ring 18 and of protecting against liquid invasion of microporous ring 17 and adhesive coating 19.

While the sealing means preferably takes the form of a hot melt sealant, other types of sealing connections might be provided.

Figure 3:
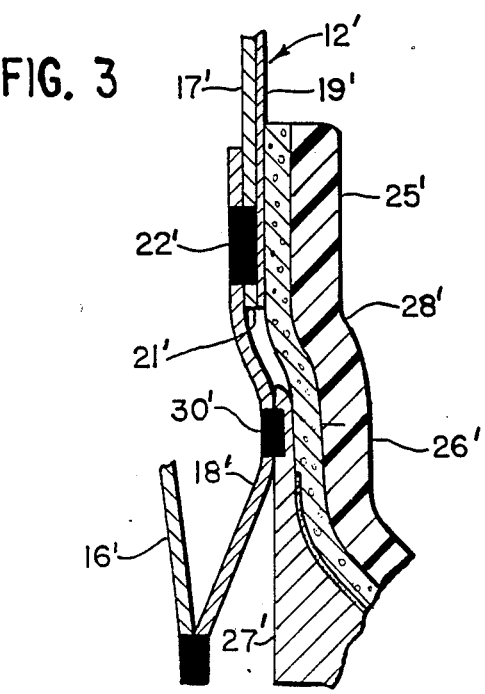
FIG. 3 is a fragmentary sectional view similar to FIG. 2, but illustrating a second embodiment of the invention.

The embodiment depicted in FIG. 3 is identical to the one already described except that the sealing means that protects the inner margin 21' of the microporous ring 17', including its adhesive coating 19', from exposure to stomal fluids takes the form of a heat seal 30' rather than a sealant ring. The annular heat seal 30' joins the impervious inner ring 18' and the barrier ring 25' along a zone radially inboard of heat seal 22'. In the illustration given, seal 30' directly joins the inner ring 18' and the distal surface of the semi-rigid pressure ring 27', but it will be understood that the sealing zone 30' might be expanded to include thermoplastic foam layer 28'.

Figure 4:
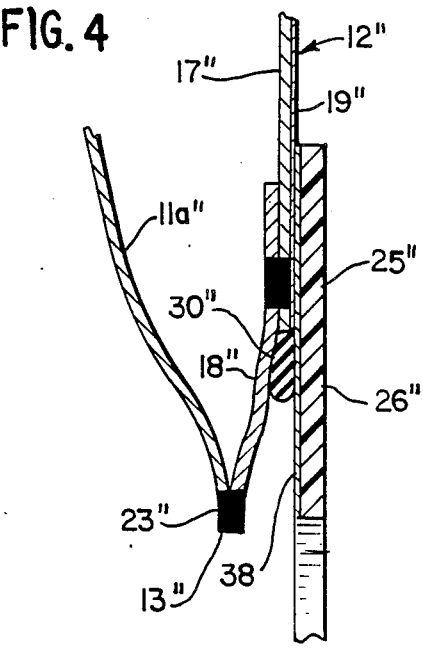
FIG. 4 is a fragmentary sectional view depicting a third embodiment of the invention.

While the protective sealing means 30 and 30' perform important functions that are specific to ostomy appliance constructions having convex pressure rings 27 and 27', it should be understood that many of the advantages of this invention may be obtained even where a pressure ring is absent. FIG. 4 illustrates a construction that is similar to the embodiments already described except that barrier ring 25" has no pressure ring or foam layer. Instead, the barrier ring 25" is composed simply of a skin barrier layer 26" backed on its distal side by a thin, fluid-impervious plastic film 38. The protective sealing means takes the form of a sealant ring 30" having a composition as disclosed in connection with the first embodiment; however, such sealant means may alternatively take the form of a heat seal of the type disclosed in connection with the second embodiment. In either case, the annular sealing means 30" joins the barrier ring 25" and the impervious inner ring 18" along an annular heat sealed zone disposed radially inwardly from the inner margin of microporous ring 17", thereby protecting that inner margin as well as the adhesive coating 19" along the proximal surface of the microporous ring from exposure to stomal fluids.

In the embodiments of FIGS. 1-3, webs 16 and 16' join the faceplate 12 and 12' to faceplate coupling rings in a manner that enhances the floating action of such rings. While the radially inward extension of inner rings 18 and 18' beyond the inner margins of the respective microporous rings contributes significantly to such floating action, important advantages of this invention may be achieved even if coupling rings are not utilized, that is, if the appliance is what is commonly referred to as a one-piece appliance. In such a construction, the heat seal 23" at the inner margin of impervious ring 18" may secure the faceplate directly to the wall 11a" of the pouch around stomal opening 13" as illustrated in FIG. 4.

While in the foregoing we have disclosed embodiments of the invention in considerable detail for purposes of illustration, it will be understood by those skilled in the art that many of these details may be varied without departing from the spirit and scope of the invention.

We claim:

1. An ostomy appliance comprising a collection pouch formed of plastic film having a wall provided with a stoma opening; a flexible and generally planar faceplate including an outer ring of thin, microporous sheet material and an inner ring of flexible sheet material impervious to gases and body fluids; said rings having coaxial openings aligned with said stoma opening and each having inner and outer margins; each of said rings also having a distal surface facing said pouch and a proximal surface facing away from said pouch; an adhesive layer on the proximal surface of said outer microporous ring; said opening of said outer microporous ring being substantially larger than said opening of said inner impervious ring; said inner impervious ring having its proximal surface adjacent the outer margin thereof secured to the distal surface of said outer microporous ring adjacent the inner margin thereof; an adhesive barrier ring secured to the proximal surface of said outer microporous ring adjacent the inner margin thereof and having a portion extending radially inwardly from said inner margin; means connecting said inner impervious ring adjacent the inner margin thereof to said pouch about said stoma opening; and annular fluid-impervious sealing means securing said proximal surface of said impervious inner ring and said inwardly extending portion of said barrier ring adjacent the inner margin of said outer microporous ring for preventing stomal fluids from contacting the inner margin of said microporous ring.

2. The appliance of claim 1 in which said annular fluid-impervious sealing means comprises a heat seal along an annular zone between said inner ring and said barrier ring.

3. The appliance of claim 1 in which said fluid-impervious sealing means comprises an adhesive sealant ring.

4. The appliance of claim 3 in which said adhesive sealant ring also sealingly and adhesively engages said outer microporous ring along the inner margin thereof.

5. The appliance of claims 3 or 4 in which said adhesive sealant ring is composed of a hot melt sealant.

6. The appliance of claim 5 in which said hot melt sealant ring is deformable and elastically recoverable.

7. The appliance of claim 1 in which said annular fluid-impervious sealing means is spaced a substantial distance radially outwardly from said inner margin of said impervious inner ring.

8. The appliance of claim 7 in which said connecting means includes an annular thermoplastic web having an inner portion sealed to said impervious inner ring adjacent the inner margin thereof and an outer portion sealed to a relatively rigid coupling ring.

9. The appliance of claim 8 in which said connecting means also includes a relatively rigid pouch coupling ring secured to said pouch about said stoma opening and detachably engaging said faceplate coupling ring.

10. The appliance of claim 1 in which said barrier ring includes a layer of soft, deformable, moisture-absorbing material having both wet and dry tack.

11. The appliance of claim 10 in which a layer of soft, resilient, liquid and gas impermeable, thermoformable material has a proximal surface sealingly engaging said layer of skin barrier material and a distal surface in sealing contact with said fluid-impervious sealing means.

12. The appliance of claim 11 in which said barrier ring also includes a relatively rigid pressure ring having a distal surface and a convex proximal surface; said fluid impervious sealing means providing a fluid-tight seal between said impervious inner ring and said distal surface of said pressure ring.

* * * * *